US012588934B1

(12) United States Patent
Pagano et al.

(10) Patent No.: US 12,588,934 B1
(45) Date of Patent: Mar. 31, 2026

(54) LUMBAR SPONDYLOLYSIS FRACTURE FIXATION SYSTEM

(71) Applicants: Paul Pagano, St. Petersburg, FL (US); Matthew D Kitzmiller, Middlefield, OH (US)

(72) Inventors: Paul Pagano, St. Petersburg, FL (US); Matthew D Kitzmiller, Middlefield, OH (US)

( * ) Notice: Subject to any disclaimer, the term of this patent is extended or adjusted under 35 U.S.C. 154(b) by 0 days.

(21) Appl. No.: 18/766,335

(22) Filed: Jul. 8, 2024

Related U.S. Application Data

(60) Provisional application No. 63/526,335, filed on Jul. 12, 2023.

(51) Int. Cl.
*A61B 17/70* (2006.01)
*A61B 17/02* (2006.01)
(Continued)

(52) U.S. Cl.
CPC ...... *A61B 17/7056* (2013.01); *A61B 17/7053* (2013.01); *A61B 17/0218* (2013.01); *A61B 2017/0256* (2013.01); *A61B 17/3417* (2013.01); *A61B 17/3439* (2013.01); *A61B 2017/3445* (2013.01); *A61B 2017/3449* (2013.01); *A61B 17/3462* (2013.01); *A61B 2017/564* (2013.01); *A61B 17/701* (2013.01); *A61B 17/7014* (2013.01); *A61B 17/7019* (2013.01); *A61B 17/7022* (2013.01); *A61B 17/7026* (2013.01); *A61B 17/7029* (2013.01); *A61B 17/7031* (2013.01); *A61B 17/7035* (2013.01);
(Continued)

(58) Field of Classification Search
CPC . A61B 17/7056; A61B 17/7053; A61B 17/70; A61B 17/701; A61B 17/7014; A61B 17/7019; A61B 17/7022; A61B 17/7026; A61B 17/7029; A61B 17/7031; A61B 17/7035; A61B 17/7043; A61B 17/7046; A61B 17/7047; A61B 17/7049; A61B 17/7062; A61B 17/7064; A61B 17/7067; A61B 17/707; A61B 17/7071; A61B 17/7074; A61B 17/7076; A61B 17/7077; A61B 17/7083; A61B 17/7085; A61B 17/7091; A61B 2017/564; A61B 2017/7073
USPC ....... 606/263, 246, 247, 248, 250, 251, 254, 606/276, 279
See application file for complete search history.

(56) References Cited

U.S. PATENT DOCUMENTS 8,617,062 B2 * 12/2013 Mire ..................... A61M 29/00
600/210
2004/0138666 A1 * 7/2004 Molz, IV .......... A61B 17/8869
606/103

(Continued)

*Primary Examiner* — Marcela I. Shirsat
(74) *Attorney, Agent, or Firm* — Rimon Law, P.C.

(57) ABSTRACT

A surgical technique for lumbar spondylolysis fracture fixation is provided. An instrumentation set for use in the method is also provided. The set includes an anchor configured to attach to a pedicle of a fractured vertebra, a flexible band configured to attach to the anchor, and a hook configured to hook under a lower lamina of a fractured vertebra and further configured to receive the flexible band. The set also includes an inserter for placing the anchor, and a tensioner device having a distal end configured to hold the hook against the lower lamina, and a proximal end configured to secure the flexible band.

10 Claims, 6 Drawing Sheets

(51) Int. Cl.
     A61B 17/34        (2006.01)
     A61B 17/56        (2006.01)

(52) U.S. Cl.
     CPC ....... *A61B 17/7043* (2013.01); *A61B 17/7046* (2013.01); *A61B 17/7062* (2013.01); *A61B 17/7064* (2013.01); *A61B 17/7067* (2013.01); *A61B 17/707* (2013.01); *A61B 17/7071* (2013.01); *A61B 2017/7073* (2013.01); *A61B 17/7074* (2013.01); *A61B 17/7083* (2013.01); *A61B 17/7091* (2013.01)

(56) References Cited

U.S. PATENT DOCUMENTS

| | | | |
|---|---|---|---|
| 2007/0239159 A1 * | 10/2007 | Altarac ............. | A61B 17/7091 606/86 A |
| 2011/0112581 A1 * | 5/2011 | Clement ........... | A61B 17/7053 606/264 |
| 2013/0072983 A1 * | 3/2013 | Lindquist .......... | A61B 17/8869 606/279 |
| 2021/0000465 A1 * | 1/2021 | Kam .................. | A61B 17/0401 |

* cited by examiner

SECTION A-A

LUMBAR SPONDYLOLYSIS FRACTURE FIXATION SYSTEM

CROSS-REFERENCE TO RELATED APPLICATIONS

This application claims the benefit of U.S. provisional patent application No. 63/526,335 filed on Jul. 12, 2023, which is incorporated herein by reference.

BACKGROUND OF THE INVENTION

Field of the Invention

The invention relates generally to the field of spinal surgery and more particularly to a fracture fixation technique for addressing lumbar spondylolysis.

Description of the Prior Art

A lumbar spondylolysis is a stress or traumatic fracture of a portion of a vertebra call the pars inter-articularis. This is a thinner portion of the vertebra that connects the anterior (front) and the posterior (back) portions of the spine together. This region of the vertebra is at higher risk of a stress type fracture due to a repetitive bending moment or secondary to a traumatic event such as a fall or impact. The incidence of this fracture is reported to occur in 6-10% of the population and most commonly occurs in the adolescent or young adult population. Patients may present with symptoms of mild to severe back pain. Some patients do not develop acute pain and remain asymptomatic throughout their life.

In order to understand this disorder and the methodology disclosed herein, a basic understanding of vertebral anatomy is needed. FIGS. 1 and 2 provide two different perspectives of a human vertebra. A pars inter-articularis fracture that allows the disconnect between the front and back portions of the spine can cause the development of a forward slippage of the upper (cranial) vertebra in relation to the lower (caudal) vertebra. This condition is called a lumbar spondylolisthesis. The loss of the stability provided by the posterior elements (bones and joints in the back portion of the spine) increases the forces experienced by the intervertebral disc and the spinal ligaments (located in the middle and front of the spine). This, in turn, can allow accelerated degeneration. If the vertebra begin to translate in relation to one another (spondylolisthesis), patients can develop progressive back pain and nerve pain due to disc degeneration and nerve compression. The progressive slippage (instability) and nerve compression may require surgical treatment in the form of a lumbar decompression and fusion. This surgical procedure has traditionally involved the removal of bone and tissue off of the nerves to make the two vertebrae grow together into one solid bone (Lumbar Fusion).

The surgical goals include stable fixation and compression of displaced or nondisplaced fractures to allow fracture healing, minimal soft tissue dissection especially in younger patients, radiographic visualization of the fracture site to monitor fracture healing, and debridement and grafting when indicated for sub-acute and chronic fractures

SUMMARY

The fracture fixation technique disclosed herein provides a minimally invasive surgical procedure requiring only small incisions and minimal muscular dissection. It is a simple technique requiring only fluoroscopy (Intraoperative Xray). The technique allows for single segment (one bone) fixation, eliminating the need for fusion to an adjacent vertebra. The technique also provides in-line compression of the fracture site via pedicle—sublaminar fixation. Pars inter-articularis anatomy is not a constraint, unlike a compression screw. Fixation, according to this method, does not limit radiograph visualization of the fracture site, and does not limit placement of graft material at the fracture site. Additionally, the technique provides a small instrumentation set with a limited number of implants and disposables.

DETAILED DESCRIPTION

The surgical technique disclosed herein includes five basic steps. An instrumentation set for lumbar spondylolysis fracture fixation is also provided. The set includes an anchor configured to attach to a pedicle of a fractured vertebra; a flexible band configured to attach to the anchor; and a hook configured to hook under a lower lamina of a fractured vertebra and further configured to receive the flexible band.

Figure 1:
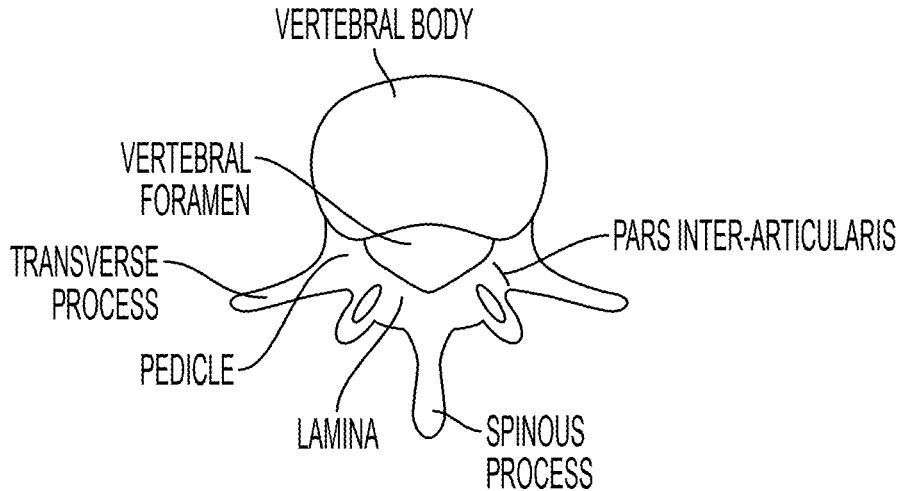
FIG. 1 is a first view of human vertebra.
Figure 2:
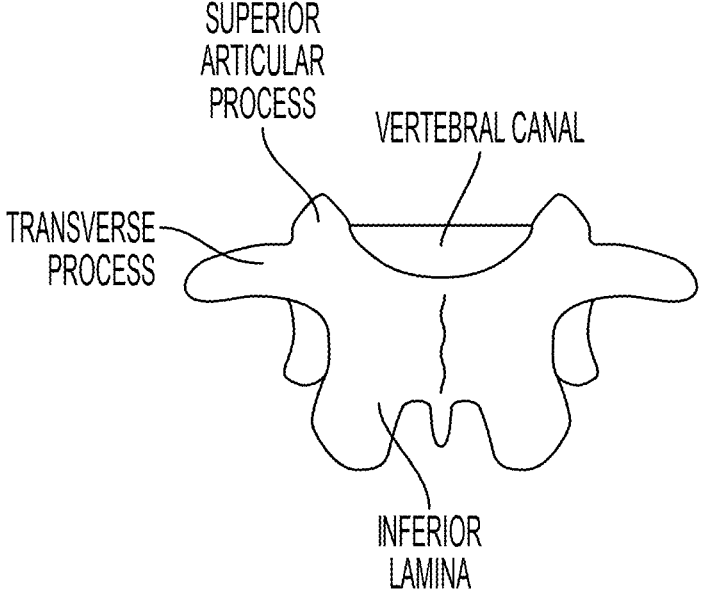
FIG. 2 is a second view of human vertebra.
Figure 3:
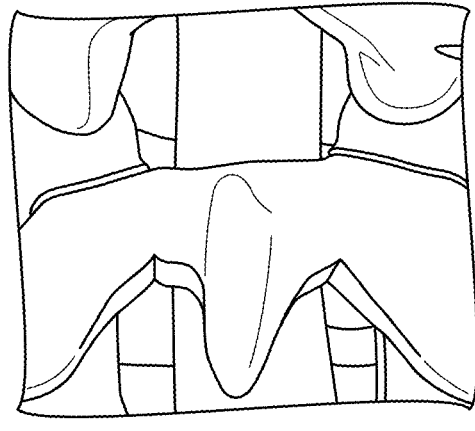
FIG. 3 illustrates a lumbar spondylolysis.

A first step comprises surgically exposing the posterior (back portion) of the fractured vertebra through a small midline incision. The inferior (lower) lamina of the fractured vertebra is identified and exposed for placement of a hook along the under surface. FIG. 3 illustrates a lumbar spondylolysis with two small notches cut to accommodate an inferior laminar hook. If the fracture is subacute to chronic the fracture (pars inter-articularis) is debrided for placement of bone graft into the fracture site later in the procedure.

Figure 4:
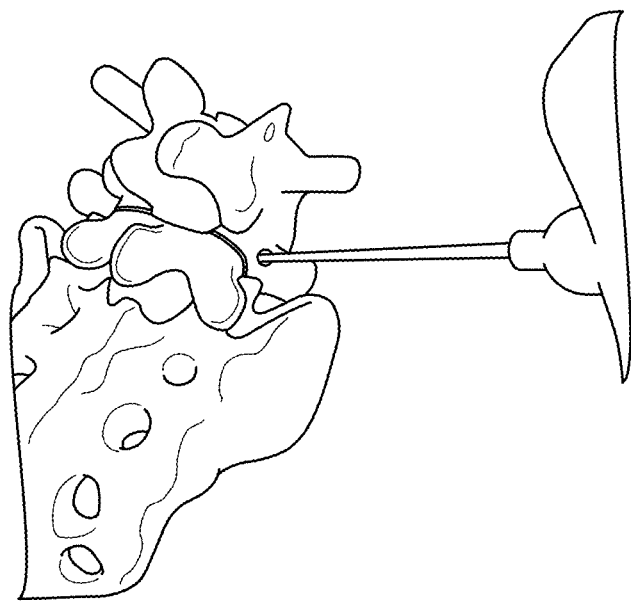
FIG. 4 depicts Jamshidi needle through the pedicle portion of a vertebra.
Figure 5:
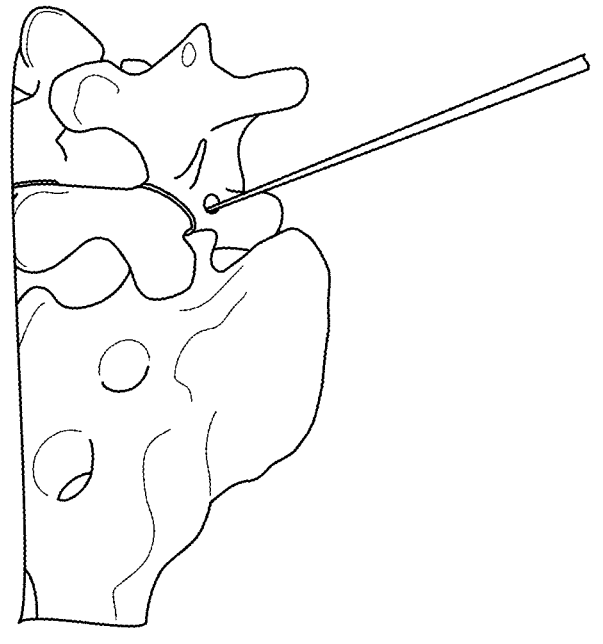
FIG. 5 shows a guidewire through the pedicle portion of a vertebra.

In a second step the pedicles are cannulated, through a small incision on the left and right sides of the midline, with a heavy trephine needle (e.g., a Jamshidi Needle) with the assistance of intraoperative fluoroscopy (Xray). This technique is commonly used to place screws into the spine through small stab incisions for a fusion. This is also a technique used to perform a Kyphoplasty procedure where bone cement is placed into a fractured vertebral body. Once the needles are positioned through the pedicle, a guide wire is then placed into the vertebral body and the needle is removed. FIG. 4 depicting Jamshidi needle through the pedicle portion of the bone and FIG. 5 shows the needle replaced with a guidewire. It should be noted that in other embodiments a tap can be placed first over the guidewire to tap the pedicle prior to placement of the screw.

The guidewire is next used to place an anchor in the pedicle. In some embodiments, the anchor is placed using a specialized inserter device, shown in two pieces in FIG. 6. The inserter allows an anchor, such as a cannulated screw, that is pivotally attached to a flexible band via a washer or loop to be placed through the small incision(s) over the guidewire without twisting. Once the anchor has been seated, the inserter allows a pull tab comprising, for example, a nitinol wire or strip that is attached to the flexible band to be percutaneously directed toward the portion of the spine exposed in the first step, without muscular dissection or disruption. Nitinol is used here as a suitable example, but the wire or strip material need not be a shape-memory alloy and only needs to be more rigid than the flexible band such that it can be easily grasped through an incision in order to pull the flexible band taut.

It should be noted that in alternative embodiments a larger incision can be employed. This embodiment may also require some additional dissection, but does not require that the anchor be placed percutaneously. The use of the inserter is optional in this embodiment.

Figure 6:
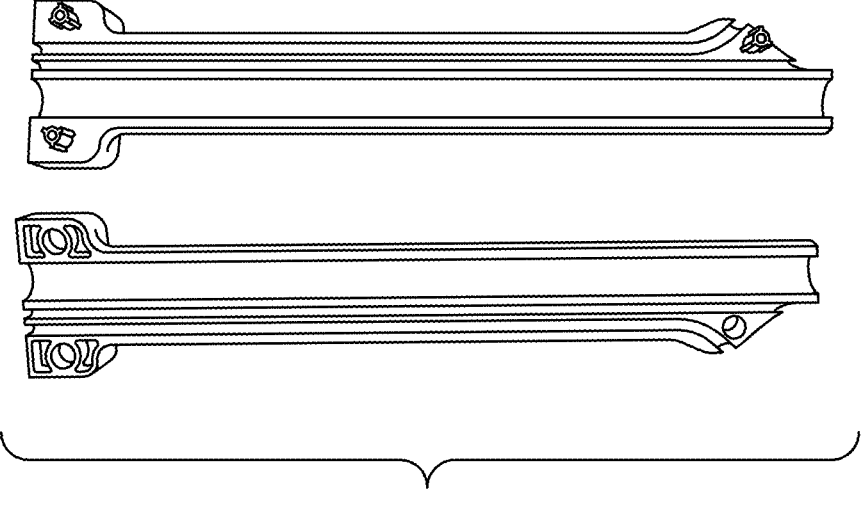
FIG. 6 shows an inserter device for placing a cannulated screw in the pedicle portion of a vertebra.
Figure 7:
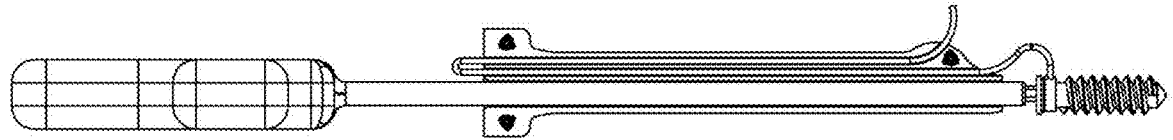
FIG. 7 is a cross sectional view of the inserter including a screw driver, pedicle screw, and a flexible band having a pull tab.

The inserter shown in FIG. 6 is made of two individual pieces and intended to be pulled apart to release the band from interior slots defined in the inserter. A suitable material for the flexible band is braided polyester. FIG. 7 is a cross section of the inserter loaded with a screw driver, pedicle screw, and the flexible band with the pull tab.

The flexible band and pull tab can consist of, for example, a nitinol strip or a nitinol wire attached to a polyester braided band. The flexible band is attached laterally to an anchor, such as a pedicle lag screw, via a small washer or loop at the end of the band, and then to a sublaminar hook medially. The pull tab is directed towards, and obtained through the midline incision. Tensioning the band provides in-line compression of the pars inter-articularis fracture.

Figure 8:
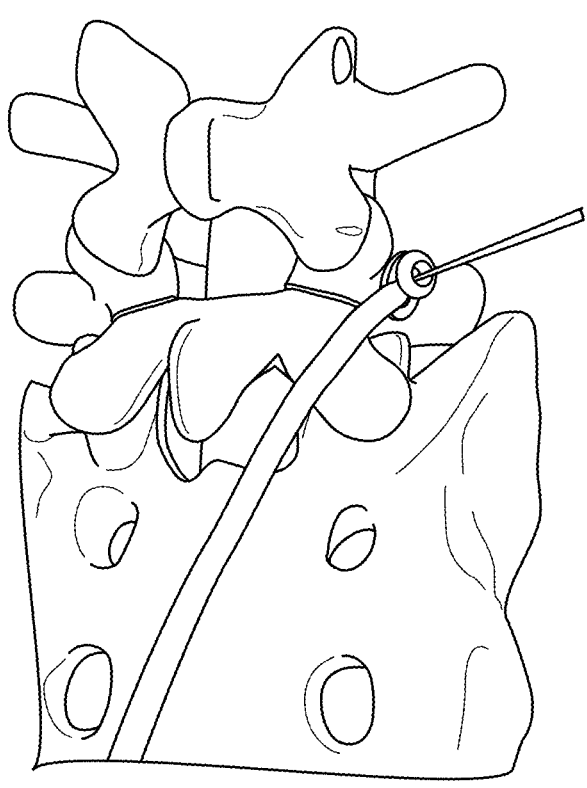
FIG. 8 shows a flexible band attached to a bone screw in the pedicle following the removal of the band from inserter.

In a third step, after the pull tab is obtained from the midline incision, the flexible band can be released from the inserter by first pulling the inserter out of the small skin incision and pulling the two sides apart. This in turn allows the band to be released from the slots inside the inserter and pulled out of the midline incision until tight. FIG. 8 shows a flexible band attached to a bone screw in the pedicle following the removal of the band from inserter.

Figure 9:
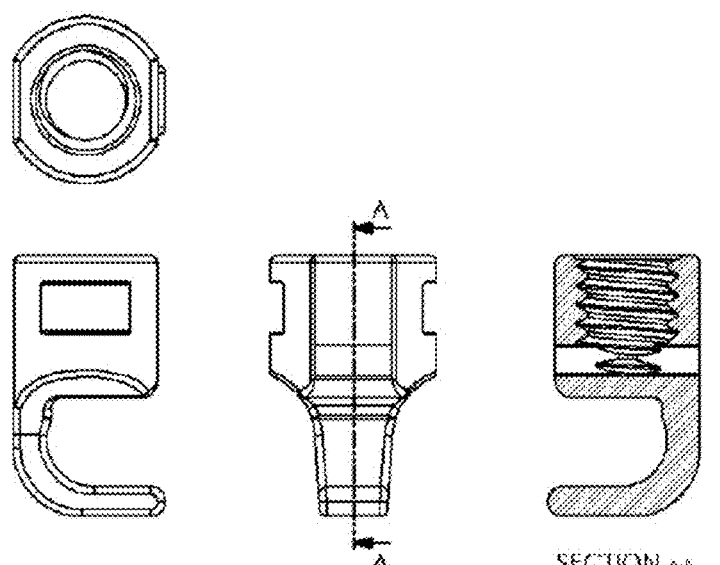
FIG. 9 shows top, front, side, and cross-sectional views of an exemplary hook.
Figure 10:
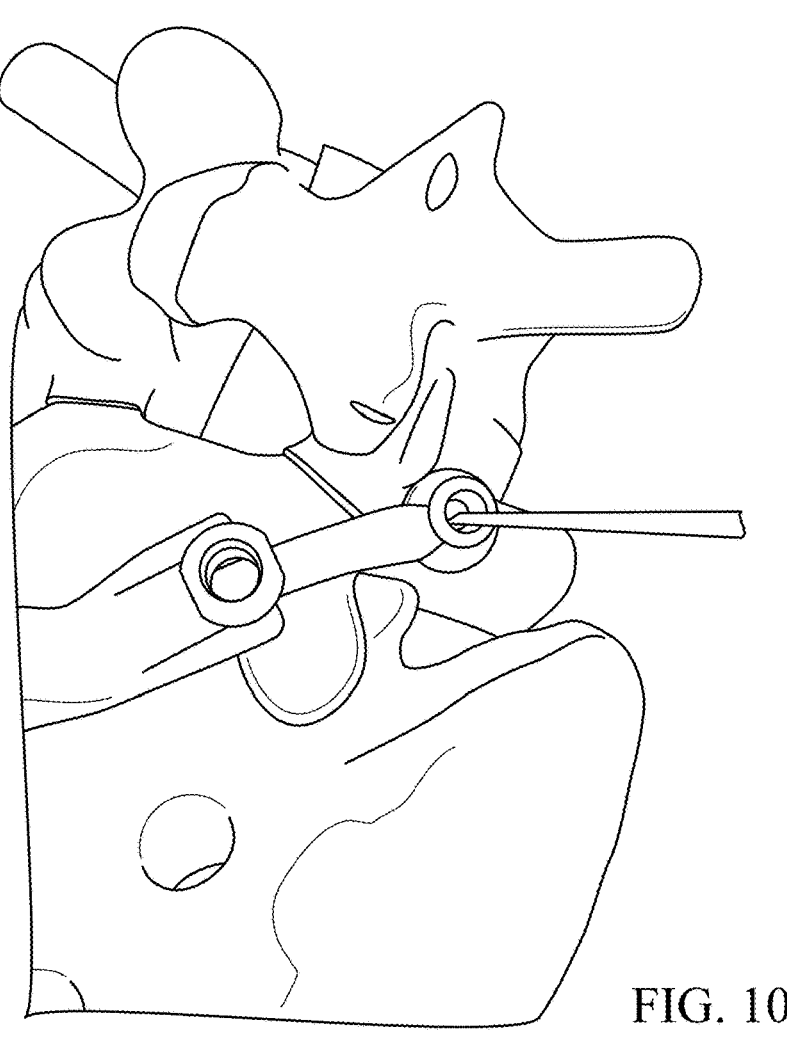
FIG. 10 shows a hook placed under the lower lamina of the fractured vertebra, with a flexible band disposed through an aperture of the hook.
Figure 11:
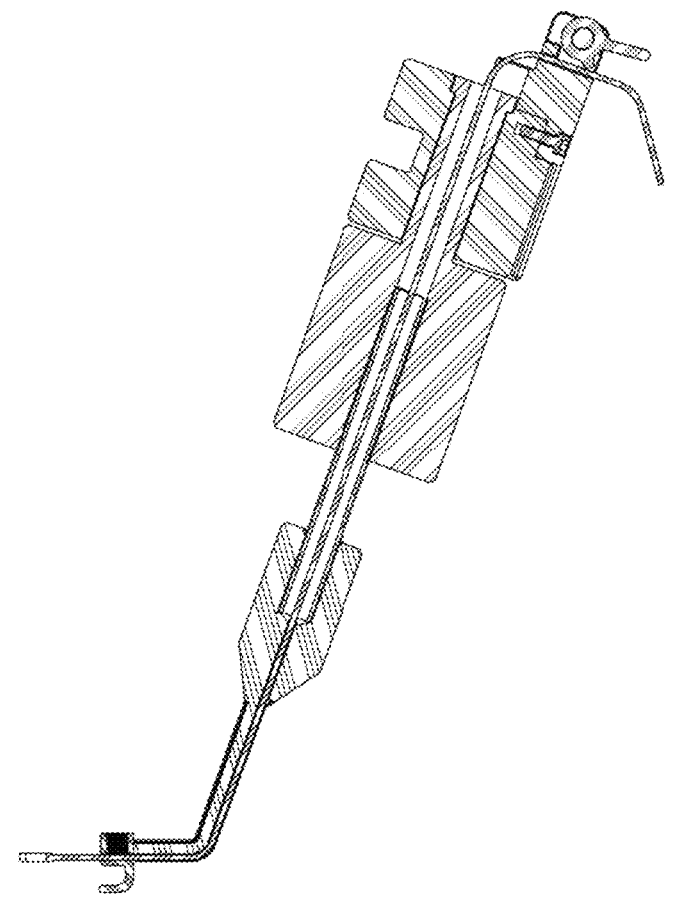
FIG. 11 is a cross-sectional view of a tensioning device retaining a hook, with a flexible band disposed through both.

In a fourth step, after the flexible band has been retrieved from the midline incision, a properly sized hook is placed under the lower lamina of the fractured vertebra. The hook is designed to accommodate and securely fixate the flexible band. FIG. 9 shows top, front, side, and cross-sectional views of an exemplary hook. The hook includes an aperture sized to receive the flexible band. FIG. 10 shows a hook placed under the lower lamina of the fractured vertebra, with the flexible band disposed through the aperture, and held in place by a tensioning device, shown in FIG. 11. The hook holder retains a hook at a distal end thereof.

In a fifth step, the flexible band is fed through the hook, then the band is fed through a channel in the holder, and then the hook is secured to the distal end. Once the hook is placed under the lower lamina the band can be pulled through the holder. To further tension the band, the band is pinched by a cam at the proximal end of the holder and the holder is caused to be elongated. In the exemplary holder of FIG. 11 a rotatable sleeve engages a threaded tube, and as the sleeve is rotated, it moves towards the proximal end, pushing the proximal end away from the distal end, drawing the band through the aperture in the hook. A ratcheting mechanism can also be used instead of the rotatable sleeve. When a proper tension has been achieved, a set screw is inserted through the top of the hook, securing the tensioned band. The band is then released from the holder and cut close to the hook. These steps are then repeated on the other side of the vertebra.

Other substitutions, modifications, changes, and omissions may also be made in the design, operating conditions, and arrangement of the various exemplary embodiments without departing from the scope of the present disclosure. Also, for example, the order or sequence of any process or method steps may be varied or re-sequenced according to alternative embodiments. Any means-plus-function clause is intended to cover the structures described herein as performing the recited function and not only structural equivalents but also equivalent structures. Other substitutions, modifications, changes, and omissions may be made in the design, operating configuration, and arrangement of the preferred and other exemplary embodiments without departing from the scope of the disclosure.

What is claimed is:

1. An instrumentation set for lumbar spondylolysis fracture fixation, the set comprising:
    an anchor configured to attach to a pedicle of a fractured vertebra;
    a flexible band configured to attach to the anchor;
    a hook configured to hook under a lower lamina of a fractured vertebra and further configured to receive the flexible band; and
    an inserter having two separable halves and including
        a first channel disposed longitudinally through the inserter and sized to receive a shaft of a screwdriver, and
        two parallel channels disposed longitudinally through the inserter on a same side of the first channel and sized to receive the flexible band.

2. The instrumentation set of claim 1 wherein the anchor comprises a bone screw.

3. The instrumentation set of claim 2 wherein a proximal end of the flexible band includes a washer or a loop configured to receive the bone screw in order to pivotally attach the flexible band to the bone screw.

4. The instrumentation set of claim 1 wherein the flexible band comprises braided polyester.

5. The instrumentation set of claim 1 wherein the flexible band includes a pull tab at a distal end thereof.

6. The instrumentation set of claim 5 wherein the pull tab comprises a nitinol wire or a nitinol strip.

7. The instrumentation set of claim 1 wherein the hook includes two opposing slots sized to receive the first flexible band therethrough, and further includes a set screw.

8. The instrumentation set of claim 1 further comprising a trephine needle adapted to bore a hole sized to receive the bone screw.

9. The instrumentation set of claim 1 further comprising a tensioner device, the tensioner device having a distal end configured to hold the hook against the lower lamina, and further having a proximal end configured to secure the flexible band.

10. The instrumentation set of claim 9 wherein the tensioner device is configured to mechanically elongate to tension the flexible band.

\* \* \* \* \*